(12) United States Patent
Matessa et al.

(10) Patent No.: US 12,042,289 B2
(45) Date of Patent: Jul. 23, 2024

(54) COGNITIVE BATTERY FOR RETURN TO SERVICE

(71) Applicant: Rockwell Collins, Inc., Cedar Rapids, IA (US)

(72) Inventors: Michael P. Matessa, Ben Lomond, CA (US); Arjun Harsha Rao, Marion, IA (US); Peggy Wu, Ellicott City, MD (US); Timothy J. Wittkop, Marion, IA (US); Christopher L George, Winchester, VA (US); Wade T. Johnson, Cedar Rapids, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 0 days.

(21) Appl. No.: 17/749,299

(22) Filed: May 20, 2022

(65) Prior Publication Data

US 2022/0386916 A1    Dec. 8, 2022

Related U.S. Application Data

(60) Provisional application No. 63/196,765, filed on Jun. 4, 2021.

(51) Int. Cl.
*G08B 23/00* (2006.01)
*A61B 5/00* (2006.01)
*A61B 5/18* (2006.01)

(52) U.S. Cl.
CPC .............. *A61B 5/18* (2013.01); *A61B 5/7267* (2013.01); *A61B 5/746* (2013.01)

(58) Field of Classification Search
CPC .......... A61B 5/18; A61B 5/7267; A61B 5/746
USPC ........................................................ 340/576
See application file for complete search history.

(56) References Cited

U.S. PATENT DOCUMENTS

| | | | |
|---|---|---|---|
| 9,867,563 B2 | 1/2018 | Peake | |
| 10,192,173 B2 | 1/2019 | Stephens et al. | |
| 10,376,198 B1 | 8/2019 | Flaherty-Woods et al. | |
| 10,426,393 B2 | 10/2019 | Bosworth et al. | |
| 2008/0122636 A1* | 5/2008 | Matos .............. | G08B 21/06 340/576 |
| 2013/0018592 A1 | 1/2013 | Mollicone et al. | |
| 2016/0332567 A1* | 11/2016 | Wilson .............. | G01S 19/14 |
| 2019/0080802 A1 | 3/2019 | Ziobro et al. | |
| 2019/0090800 A1 | 3/2019 | Bosworth et al. | |

(Continued)

FOREIGN PATENT DOCUMENTS

WO    2005023112 A1    3/2005

OTHER PUBLICATIONS

Extended Search Report in European Application No. 22177250.2 dated Oct. 7, 2022, 14 pages.

*Primary Examiner* — Naomi J Small
(74) *Attorney, Agent, or Firm* — Suiter Swantz IP

(57) ABSTRACT

A computerized system for recognizing the need for cognitive tests due to a physiological event and administering such tests includes a plurality of biometric monitoring devices and a pilot input device. When a physiological event is identified, the system selects an appropriate battery of tests and automatically administers those tests. The system offers the opportunity to automate pilot evaluation for single pilot operations, and to reduce the burden on a co-pilot. The cognitive tests may be specific to the physiological event, and may be compared to a pilot-specific profile when evaluating the results.

17 Claims, 2 Drawing Sheets

(56) References Cited

U.S. PATENT DOCUMENTS

| | | |
|---|---|---|
| 2021/0034053 A1 | 2/2021 | Nikolic et al. |
| 2021/0291650 A1* | 9/2021 | Minjeur ................. B60R 11/04 |
| 2022/0153302 A1* | 5/2022 | Arechiga-Gonzalez .................... B60W 50/14 |
| 2023/0058169 A1* | 2/2023 | Cella ...................... G06N 3/126 |

* cited by examiner

COGNITIVE BATTERY FOR RETURN TO SERVICE

PRIORITY

The present application claims the benefit under 35 U.S.C. § 119(e) of U.S. Provisional App. No. 63/196,765 (filed Jun. 4, 2021), which is incorporated herein by reference.

BACKGROUND

Currently, the ability of a pilot to return to service after a physiological event is determined by a co-pilot. That methodology is slow, subjective, prone to human error, and places an additional burden on the co-pilot at precisely the time when that additional burden is unsupportable. Furthermore, during single pilot operations, there is no individual that can administer a cognitive test for return to service.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
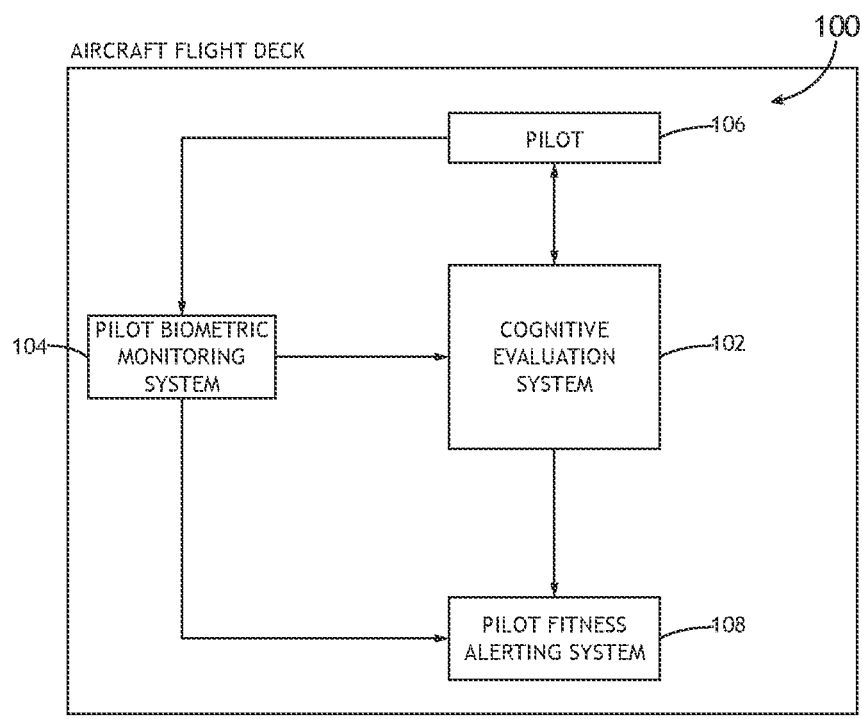
FIG. 1 shows a block diagram of pilot monitoring system according to an exemplary embodiment.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a" and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a computerized system for recognizing the need for cognitive tests due to a physiological event and administering such tests. The system offers the opportunity to automate pilot evaluation for single pilot operations, and to reduce the burden on a co-pilot. The cognitive tests may be specific to the physiological event, and may be compared to a pilot-specific profile when evaluating the results.

Embodiments of the present disclosure may be more fully understood with reference to U.S. Patent App. No. 63/196,784 ("Physiological and Behavioural Methods to Assess Pilot Readiness") (filed Jun. 4, 2021) and U.S. Patent App. No. 63/196,798 ("Embedding Sensors in an Aircraft Control") (filed Jun. 4, 2021).

Referring to FIG. 1, a block diagram of pilot monitoring system 100 according to an exemplary embodiment is shown. The system 100 includes a cognitive evaluation system 102 including a processor and memory connected to the processor for embodying processor executable code. The cognitive evaluation system 102 is in data communication with a biometric monitoring system 104. The biometric monitoring system 104 includes a plurality of biometric monitoring sensors such as a pulse sensor, an $O_2$ sensor, an electroencephalogram sensor, an electrocardiogram sensor, one or more vision-based sensors, etc. In at least one embodiment, the biometric monitoring system 104 may include a separate processor configured to pre-process inputs from the biometric sensors and deliver data streams to the cognitive evaluation system 102.

The biometric monitoring system 104 continuously receives biometric data from a pilot 106. The cognitive evaluation system is configured to analyze the biometric data streams to identify physiological events in the pilot that may be impairing or incapacitating. For example, the cognitive evaluation system 102 may identify hypoxia in the pilot 106 with reference to an $O_2$ sensor. It may be appreciated that electroencephalogram sensors and electrocardiogram sensors are highly sensitive to changes in the pilot's limbic system which may indicate changes to the pilot's cognitive state.

Upon identifying a physiological event that may impair or incapacitate the pilot 106, the cognitive evaluation system 102 may send a signal to a pilot fitness alerting system 108 configured to provide a warning message to the pilot 106, other crew members, flight or ground control, etc. If the pilot 106 believes he or she is fit for duty, the cognitive evaluation system 102 may administer a set of tests to objectively determine if the pilot 106 is sufficiently unimpaired for duty.

In at least one embodiment, the cognitive evaluation system 102 identifies a set of tests specific to the physiological event. The cognitive evaluation system 102 administers the set of tests and receives responses from the pilot 106. In at least one embodiment, the biometric monitoring system 104 is configured to monitor the pilot 106 while responding to the tests, and includes the received biometric data when evaluating test responses.

After the tests are administered, the pilot fitness alerting system 108 reports the pilot's fitness for duty to the pilot and ground support.

Figure 2:
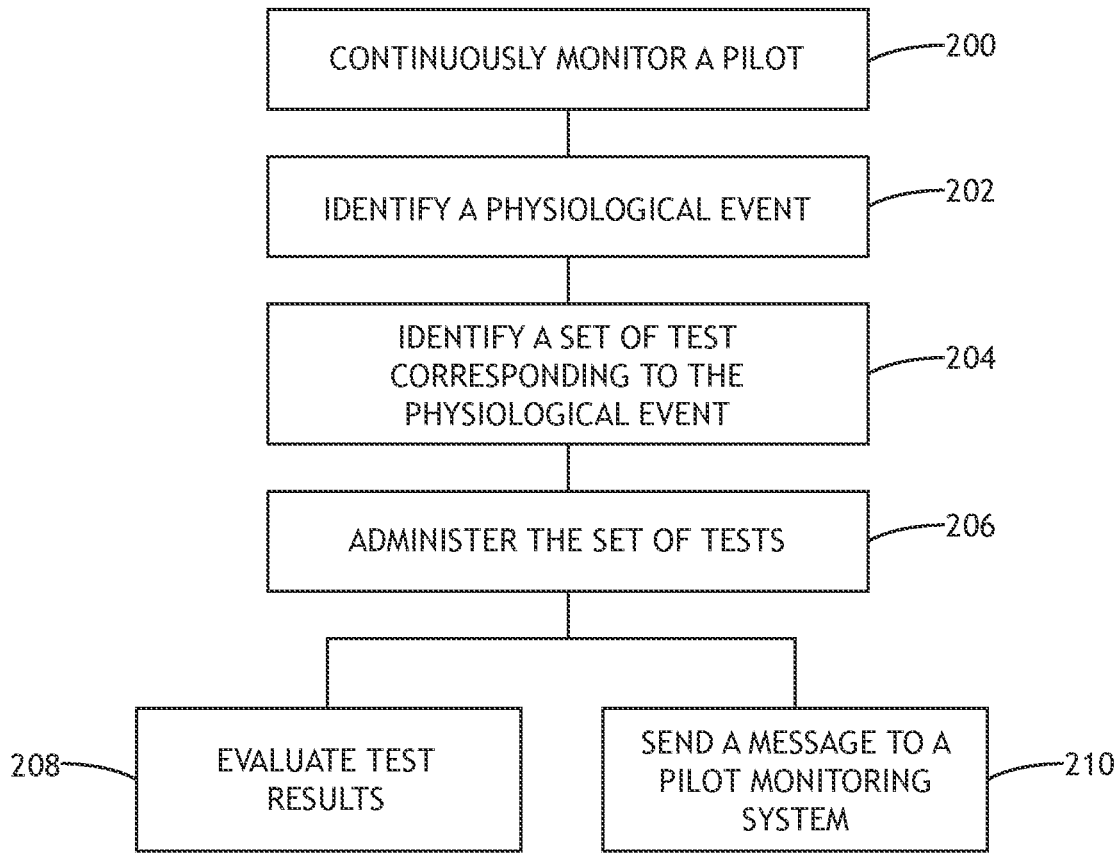
FIG. 2 shows a flowchart of a pilot monitoring process according to an exemplary embodiment.

Referring to FIG. 2, a flowchart of a pilot monitoring process according to an exemplary embodiment is shown. A processor in data communication with a plurality of biometric sensors continuously monitors 200 a pilot. When a physiological event is identified 202, the processor identifies 204 a set of tests specific to the physiological event and administers 206 the tests to the pilot. In at least one embodiment, biometric data from the pilot is analyzed in concert with the test results to provide additional objective pilot fitness verification.

In at least one embodiment, the methodology of identifying a physiological event may comprise monitoring for certain biometric thresholds. Alternatively, or in addition, identifying a physiological event may comprise a weighted analysis of multiple biometric factors such as via a trained neural network or other machine intelligence. Likewise, identifying 204 a set of tests may comprise selecting a defined set of tests according to each identified physiological event, or selecting tests based on some machine intelligence implemented algorithm. Tests may be selected based on prior test responses or biometric data gathered during test administration, or both.

The processor evaluates 208 the pilot's responses to determine the pilot's fitness for duty. Such evaluation 208 may be comprise a simple comparison of desired responses with actual responses. Alternatively, such evaluation 208 may comprise a weighted analysis of multiple biometric factors such as via a trained neural network or other machine intelligence, test responses, and response time. For example, a correct response to a simple question, accompanied by a biometric indication of extreme concentration and a long dwell time on the question, may indicate continued cognitive impairment.

In at least one embodiment, the processor sends 210 a signal to a pilot monitoring system which may send a message to the pilot, other crewmembers, and a ground or flight controller indicating the results of the evaluation 208.

Embodiments of the present disclosure enable a computerized cognitive testing system to determine a pilot's mental capabilities after a physiological event. The system consists of a number of tests to evaluate particular cognitive functions. These tests can be selected to evaluate general functionality or can be chosen to be relevant to the physiological event. The system provides an objective measure of pilot cognitive capability, which would enable certain single pilot operations.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
    a pilot display device;
    a pilot input device; and
    at least one processor in data communication with a plurality of biometric sensors including at least an $O_2$ sensor, an electroencephalogram sensor, and an electrocardiogram sensor, the pilot display device, the pilot input device, and a memory storing processor executable code for configuring the at least one processor to:
        continuously receive data streams from each of the biometric sensors;
        identify a physiological event of a pilot based on the data streams;
        distinguish the physiological event from a set of physiological events including at least hypoxia and cognitive impairment based on data from the $O_2$ sensor, an electroencephalogram sensor, and an electrocardiogram sensor;
        retrieve a set of tests to evaluate a cognitive state of the pilot, the set of tests being content specific to the identified physiological event;
        administer the set of tests to the pilot and receive corresponding responses; and
        determine the pilot's cognitive fitness for duty based on the pilot's responses to the set of tests.

2. The computer apparatus of claim 1, wherein the at least one processor is further configured to communicate the determined fitness for duty to the pilot and a ground controller.

3. The computer apparatus of claim 1, wherein the at least one processor is further configured to:
    alert the pilot of the physiological event; and
    receive an affirmation from the pilot that the pilot is fit for duty prior to administering the set of tests.

4. The computer apparatus of claim 1, wherein the at least one processor is further configured to continuously receive data streams from each of the biometric sensors while administering the set of tests.

5. The computer apparatus of claim 4, wherein determining the pilot's cognitive fitness for duty further comprises monitoring the data streams during the pilot responses to the set of tests.

6. The computer apparatus of claim 1, wherein at least one of the at least one processors is configured to instantiate a trained neural network to identify the physiological event and determine the pilot's cognitive fitness for duty.

7. A method for evaluating pilot readiness comprising:
    continuously receiving data streams from each of the biometric sensors including at least an $O_2$ sensor, an electroencephalogram sensor, and an electrocardiogram sensor;
    identifying a physiological event of a pilot based on the data streams;
    distinguishing the physiological event from a set of physiological events including at least hypoxia and cognitive impairment based on data from the $O_2$ sensor, an electroencephalogram sensor, and an electrocardiogram sensor;

alerting the pilot of the physiological event;
receiving an affirmation from the pilot that the pilot is fit for duty prior to administering the set of tests;
retrieving a set of tests to evaluate a cognitive state of the pilot, the set of tests being content specific to the identified physiological event;
administering the set of tests to the pilot and receive corresponding responses; and
determining the pilot's cognitive fitness for duty based on the pilot's responses to the set of tests.

8. The method of claim 7, further comprising communicating the determined fitness for duty to the pilot and a ground controller.

9. The method of claim 7, further comprising continuously receiving data streams from each of the biometric sensors while administering the set of tests.

10. The method of claim 9, wherein determining the pilot's cognitive fitness for duty further comprises monitoring the data streams during the pilot responses to the set of tests.

11. The method of claim 7, further comprising instantiating a trained neural network to identify the physiological event and determine the pilot's cognitive fitness for duty.

12. A system for evaluating pilot readiness comprising:
a plurality of biometric sensors including at least an $O_2$ sensor, an electroencephalogram sensor, and an electrocardiogram sensor;
a pilot display device;
a pilot input device; and
at least one processor in data communication with the plurality of biometric sensors, the pilot display device, the pilot input device, and a memory storing processor executable code for configuring the at least one processor to:
continuously receive data streams from each of the biometric sensors;
identify a physiological event of a pilot based on the data streams;
distinguish the physiological event from a set of physiological events including at least hypoxia and cognitive impairment based on data from the $O_2$ sensor, an electroencephalogram sensor, and an electrocardiogram sensor;
retrieve a set of tests to evaluate a cognitive state of the pilot, the set of tests being content specific to the identified physiological event;
administer the set of tests to the pilot and receive corresponding responses; and
determine the pilot's cognitive fitness for duty based on the pilot's responses to the set of tests.

13. The system of claim 12, wherein the at least one processor is further configured to communicate the determined fitness for duty to the pilot and a ground controller.

14. The system of claim 12, wherein the at least one processor is further configured to:
alert the pilot of the physiological event; and
receive an affirmation from the pilot that the pilot is fit for duty prior to administering the set of tests.

15. The system of claim 12, wherein the at least one processor is further configured to continuously receive data streams from each of the biometric sensors while administering the set of tests.

16. The system of claim 15, wherein determining the pilot's cognitive fitness for duty further comprises monitoring the data streams during the pilot responses to the set of tests.

17. The system of claim 12, wherein the at least one processor is further configured to instantiate a trained neural network to identify the physiological event and determine the pilot's cognitive fitness for duty.

* * * * *